(12) United States Patent
Jiang et al.

(10) Patent No.: US 9,382,546 B2
(45) Date of Patent: Jul. 5, 2016

(54) PROCESS FOR MAKING OLIGOPEPTIDES

(75) Inventors: Shisong Jiang, Oxford (GB); Ruth Ruprecht, Boston, MA (US)

(73) Assignees: ISIS INNOVATION LTD., Oxfordshire (GB); DANA-FARBER CANCER INSTITUTE, INC., Boston, MA (US)

( * ) Notice: Subject to any disclaimer, the term of this patent is extended or adjusted under 35 U.S.C. 154(b) by 665 days.

(21) Appl. No.: 12/298,835

(22) PCT Filed: Apr. 30, 2007

(86) PCT No.: PCT/GB2007/050225
§ 371 (c)(1),
(2), (4) Date: Feb. 6, 2009

(87) PCT Pub. No.: WO2007/125371
PCT Pub. Date: Nov. 8, 2007

(65) Prior Publication Data
US 2010/0291061 A1 Nov. 18, 2010

(30) Foreign Application Priority Data
Apr. 28, 2006 (GB) .................................. 0608368.7

(51) Int. Cl.
*A61K 38/00* (2006.01)
*C12N 15/62* (2006.01)
*C07K 14/005* (2006.01)

(52) U.S. Cl.
CPC .............. *C12N 15/62* (2013.01); *C07K 14/005* (2013.01); *C07K 2319/50* (2013.01); *C12N 2740/16322* (2013.01)

(58) Field of Classification Search
None
See application file for complete search history.

(56) References Cited

U.S. PATENT DOCUMENTS 5,795,974 A * 8/1998 Cole et al. ..................... 536/23.7
6,858,410 B2 * 2/2005 Hoess et al. .................. 435/71.1

FOREIGN PATENT DOCUMENTS

| SE | WO0116163 A2 * | 3/2001 | ............. C07K 14/02 |
| WO | 96/32468 A2 | 10/1996 | |
| WO | WO 01/16163 * | 3/2001 | |
| WO | 2004/002415 A2 | 1/2004 | |

OTHER PUBLICATIONS

Leyte A. et al. "Inhibition of human coagulation Factor VIII by monoclonal antibodies" Biochem. 263:187-194, 1989.*
KM Weeks, et al. "Fragments of the HIV-1 Tat protein specifically bind TAR RNA" Science, Sep. 14, 1990: vol. 249 No. 4974 pp. 1281-1285.*

Leyte A et al. Inhibition of human coagulation factor VIII by monoclonal antibodies. Mapping of functional epitopes with the use of recombinant factor VIII fragments. Biochem J. Oct. 1, 1989;263(1):187-94.*
Lindhout et al. High-yield expression of isotopically labeled peptides for use in NMR studies. Protein Sci. Aug. 2003; 12(8): 1786-1791.*
Andersen et al. The universal character of the tumor-associated antigen survivin. Clin Cancer Res. Oct. 15, 2007;13(20):5991-4.*
Ayyavoo, V. et al., "Immunogenicity of a novel DNA vaccine cassette expressing multiple human immunodeficiency virus (HIV-1) accessory genes," AIDS (London, England), Jan. 7, 2000, vol. 14, No. 1, pp. 1-9.
Draenert, R. et al., "Comparison of overlapping peptide sets for detection of antiviral CD8 and CD4 T cell responses," Journal of Immunological Methods, Apr. 1, 2003, vol. 275, Nos. 1-2, pp. 19-29.
WO 2007/125371 A3—International Search Report, International Application No. PCT/GB2007/050225, dated Jan. 8, 2008, 5 pages.
English translation of Second Office Action for CN Application No. 200780024534.6, Issued Mar. 27, 2012, Applicant: Isis Innovation Limited, Title: Process for Making Oligopeptides, 13 pages.
Ronghong Hua et al., "The Expression of SARS Coronavirus S Protein Receptor Binding Domain and the Epitope Mapping Thereof," Progress in Biochemistry and Biophysics, vol. 32, Issue 11, Dec. 31, 2005, pp. 1031-1037.

(Continued)

*Primary Examiner* — Nick Zou
(74) *Attorney, Agent, or Firm* — Rothwell, Figg, Ernst & Manbeck P.C.

(57) ABSTRACT

There is described a method of synthesizing a family of oligopeptides of predetermined amino acid sequence, which together make up from 7 amino acids to the complete amino acid sequence of a target protein, which comprises: synthesizing a nucleic acid construct which codes for a fusion protein composed of overlapping peptides derived from the desired portion of the target protein, interspersed with regions which code for protease cleavage sites, expressing the nucleic acid construct in a suitable expression vector, harvesting the fusion protein corresponding to the nucleic acid sequence, and digesting the fusion protein with a protease selective for the cleavage sites to generate the oligopeptides. The oligopeptides may be generated in vitro or in vitro and may be used as vaccines against viral infections and in epitope mapping.

MGGKWSKSSVVGWPAVRERMIEGRVGWPAVRERMRRAEPAADGVIEGRRRA

EPAADGVGAVSRDLEKHIEGRGAVSRDLEKHGAITSSNTAAIEGRGAITSS

NTAATNADCAWLEAIEGRTNADCAWLEAQEEEEVGFPVIEGRQEEEEVGFP

VTPQVPLRPMTIEGRTPQVPLRPMTYKAAVDLSHFIEGRYKAAVDLSHFLK

EKGGLEGLIEGRLKEKGGLEGLIHSQRRQDILIEGRIHSQRRQDILDLWIY

HTQGYIEGRDLWIYHTQGYFPDWQNYTPEIEGRFPDWQNYTPEPGVRYPLT

FGIEGRPGVRYPLTFGWCY

11 Claims, 8 Drawing Sheets

(56) References Cited

OTHER PUBLICATIONS

Ronghong Hua et al., "Expression and Antigenic Epitopes Mapping of Receptor Binding Domain on the Spike Protein of Severe Acute Respiratory Syndrome Coronavirus," (Abstract only), 1 page.

Decision on Rejection, State Intellectual Property Office, People's Republic of China, Chinese Application No. 200780024534.6, "Process for Making Oligopeptides," Filing date: Apr. 30, 2007, Priority date: Apr. 28, 2006, Applicant: Isis Innovation Limited, Date of Issue: Dec. 28, 2012, 24 pages.

\* cited by examiner

MGGKWSKSSVVGWPAVRERMIEGRVGWPAVRER
MRRAEPAADGVIEGRRRAEPAADGVGAVSRDLEK
HIEGRGAVSRDLEKHGAITSSNTAAIEGRGAITSSN
TAATNADCAWLEAIEGRTNADCAWLEAQEEEEVG
FPVIEGRQEEEEVGFPVTPQVPLRPMTIEGRTPQVP
LRPMTYKAAVDLSHFIEGRYKAAVDLSHFLKEKG
GLEGLIEGRLKEKGGLEGLIHSQRRQDILIEGRIHSQ
RRQDILDLWIYHTQGYIEGRDLWIYHTQGYFPDWQ
NYTPEIEGRFPDWQNYTPEPGVRYPLTFGIEGRPG
VRYPLTFGWCY

Fig. 1

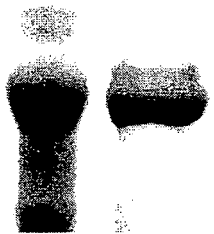

Fig. 2

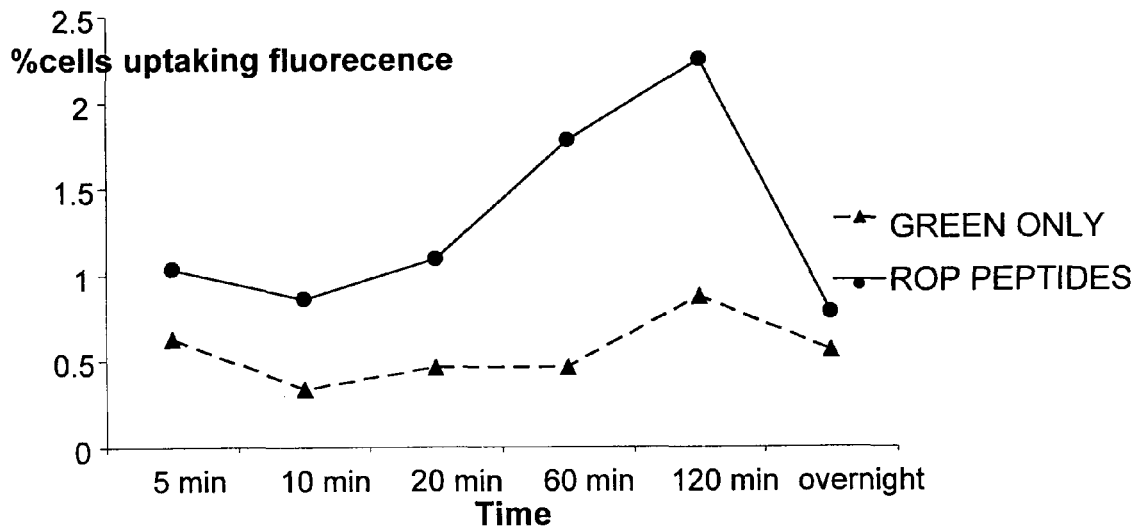
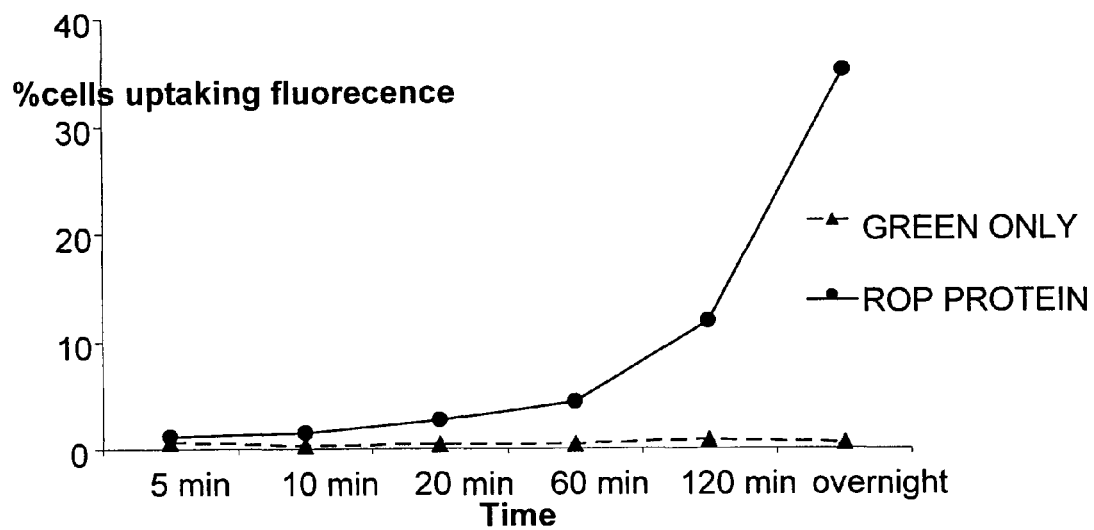
Fig.4

Fig. 5

PROCESS FOR MAKING OLIGOPEPTIDES

CROSS-REFERENCE TO RELATED APPLICATIONS

The present application is a national stage filing under 35 U.S.C. §371 of PCT/GB2007/050225, filed on 30 Apr. 2007 which in turn claims priority to United Kingdom Patent Application No. GB 0608368.7, filed on 28 Apr. 2006. The disclosures of each of the above applications are hereby incorporated by reference in their entireties into the present application.

This invention relates to a process of making recombinant overlapping peptides, in particular recombinant overlapping peptides for use in the preparation of a vaccine for the prevention and treatment of viral infections and tumours.

WO 01/16163 discloses oligopeptide mixtures, comprising a mixture of 10 to 30 amino acids oligopeptides, each with a 5 to 25 amino acid overlap of the adjacent overlapping peptide spanning the amino acid sequence of a viral protein of a virus, for example Hepatitis B. According to this patent application, a peptide mixture composed of seventeen 20 to 23 amino acids oligopeptides spanning the amino acids 1 to 183 of the hepatitis B core antigen (HbcAg) could activate specific T cells regardless of the host MHC/HLA genotype that recognize the native protein processed by professional antigen presenting cells (APCs). The overlapping peptides exemplified are synthesised using standard chemical techniques using an automated synthesizer. These techniques are slow, low yielding and not well adapted to rapid scale up. The use of short peptide fragments, which may be overlapping or contiguous, as vaccines are also described in WO2004/002415.

We have now found a new method for synthesising oligopeptides for use in the vaccination methods described above which overcomes the problems associated with the conventional chemical synthesis and offers the possibility of rapid generation of a family of oligopeptides on a commercial scale.

According to one aspect of the invention we provide a method of synthesising a family of oligopeptides of predetermined amino acid sequence, which together make up from 7 amino acids to the complete amino acid sequence of a protein, which comprises:
synthesising a nucleic acid construct which codes for a fusion protein composed of overlapping peptides derived from the desired portion of the protein, interspersed with regions which code for protease cleavage sites, expressing the nucleic acid sequence in a suitable expression vector, harvesting the protein corresponding to the nucleic acid sequence, and digesting the protein with a protease selective for the cleavage sites to generate the oligopeptides.

According to a second aspect of the invention we provide a method of synthesising a family of oligopeptides of predetermined amino acid sequence, which together make up from 7 amino acids to the complete amino acid sequence of a target protein, which comprises:
synthesising a nucleic acid construct which codes for a fusion protein composed of overlapping peptides derived from the desired portion of the target protein, interspersed with regions which code for protease cleavage sites, introducing the nucleic acid construct into a suitable vector, inducing expression of the fusion protein by a host cell, whereby the expressed fusion protein is cleaved intracellularly by a host protease or a non-host protease encoded by the same or different vector, the protease being selective for the cleavage sites, to generate the oligopeptides, and harvesting the oligopeptides.

The oligopeptides produced by the methods of the invention may be administered as vaccines to humans or animals.

According to a third aspect the invention provides a fusion protein composed of overlapping peptides derived from a desired portion of a target protein interspersed with regions which code for protease cleavage sites. This may be directly administered alone or in combination with a protease to humans or animals as a vaccine.

The oligopeptides making up the desired sequence of the target protein may be either contiguous or overlapping. Preferably the oligopeptides comprise a mixture of 10 to 30 amino acids long oligopeptides each with a 5 to 25 amino acid overlap with the adjacent overlapping peptide spanning the amino acid sequence of the target protein.

The oligopeptides are preferably of equal length, but can differ in length.

The protease cleavage site may be any amino acid sequence which is selectively digested by a protease. The cleavage site may be of any length. Preferably, the cleavage site is less than ten amino acids, more preferably less than eight amino acids, most preferably less than six amino acids in length. We particularly prefer the protease cleavage site to be a Factor Xa digestion site, that is, the sequence Ile-Glu-Gly-Arg- (SEQ ID NO:1). This sequence is cleaved after the Arg. Other proteases that may be mentioned include HRV 3 C protease, which cleaves the sequence Leu-Glu-Val-Leu-Phe-Gln/Gly-Pro- (SEQ ID NO:2) between the glutamyl and glycyl residues; the HIV protease; metalloproteinases, tryptases and other proteases such as cathepsins (S, L and B etc) CD13 (human aminopeptidase N).

Publications relating to carthepsins and their specificity as proteases include:
Ruckrich, T., J. Brandenburg, A. Cansier, M. Muller, S. Stevanovic, K. Schilling, B. Wiederanders, A. Beck, A. Melms, M. Reich, C. Driessen, and H. Kalbacher. 2006. Specificity of human cathepsin S determined by processing of peptide substrates and MHC class II-associated invariant chain. Biol Chem 387: 1503.
Choe, Y., F. Leonetti, D. C. Greenbaum, F. Lecaille, M. Bogyo, D. Bromme, J. A. Ellman, and C. S. Craik. 2006. Substrate profiling of cysteine proteases using a combinatorial peptide library identifies functionally unique specificities. J Biol Chem 281: 12824.

In addition to the above-mentioned literature, the cathepsin S sequence TVQ/L (SEQ ID NO:3) ("/" represents the cutting site) is particularly preferred.

The target protein may be any protein, which may for example be selected according to the disease to be treated or prevented. Typically, the target protein will be a characteristic of the virus responsible for the disease to be treated, e.g a coat protein of the virus or enzyme characteristic of the virus.

For example, in HIV infections, either the HIV Nef or HIV Gag proteins may be selected as the target protein; in influenza, the target protein could be a hemoglutinin, neuraminidase, nucleoprotein or matrix protein; in colon cancer, the target protein could be carcinoembryonic antigen; in breast cancer, Her2/neu antigen.

Preferably the family of oligopeptides together make up 100% the complete amino acid sequence but could be as few as 7 amino acids of the target protein. In general we prefer the family of oligopeptides to make up at least 50%, more preferably 75% of the complete amino acid sequence of the target protein. The nucleic acid construct which codes for the desired portion of the target protein interspersed with regions which code for protease cleavage sites may be synthesised by commercially available technologies, eg GeneArt™, GeneMaker™, GenScript™.

Suitable expression vehicles for amplifying the construct are preferably prokaryotic expression vector pET 16 when Factor Xa is used for protein digestion. Alternative expression systems could be other prokaryotic expression vectors, such as other pET series vectors, pGEX, pGEMT7, mammalian expression vectors such pEGFP, pcDNA3, pCDM7, or insect expression vectors such as Bac-To-Bac, BaculoDirect.

Suitable vehicles for expressing the target protein coded by the construct will be applied accordingly, e.g. *E. coli* BL21 for prokaryotic expression, HEK293T cells, HELA cells, etc for mammalian expression, sf9 cells etc for insect expression.

According to the first aspect of the invention the fusion protein may be harvested and purified using standard methods, e.g. in the case of pET16 prokaryotic system, protein expression will be induced by IPTG (isopropyl-beta-D-thiogalactopyranoside), and the protein purified from the cell lysate by affinity chromatography, preferably Ni-NTA column. Following digestion by specific protease, which is normally commercially available, e.g. Factor Xa (Merck Novagen), oligopeptide will be further purified by standard techniques, e.g. high performance liquid chromatography (HPLC), ion exchange chromatography, gel filtration chromatography.

More specifically, the oligopeptides may be prepared in vitro as follows:

1. Design and Generation of the Synthetic Gene

A synthetic gene consisting of 20mer overlapping peptides from the original target gene can be designed with protease Factor Xa sites added in between the 20mer peptides. The resultant artificial gene can be optimised for *E. coli*. expression and commercially synthesised before being cloned into prokaryotic expression vector such as pET16.

2. Protein Expression, Digestion and Purification In Vitro

The construct with the artificial gene can be expressed in *E. Coli*. BL21 as inclusion bodies, which can be purified, and the protein completely digested with protease Factor Xa. The resultant 24mer peptides (20mer from the target vaccine gene plus 4mer Factor Xa recognition site) can be purified, e.g. by High Performance Liquid Chromatography (HPLC).

Alternatively, the fusion protein containing protease cleavage sites can be directly administered as a vaccine. It will be cleaved by a protease inside the body or a protease administered separately or together with the fusion protein.

According to the second aspect of the invention the nucleic acid sequence may be expressed in a host cell using any of the expression vectors and systems described above.

Alternatively, the nucleic acid sequence may be expressed by a bacterial or viral vector within a host cell which has been infected by the virus or bacterium. Preferred bacterial vectors are *Listeria, Salmonella*, and *Shigella*. Preferred viral vectors are adenovirus, poxvirus, lentivirus and alphavirus, etc. *Listeria* vectors are particularly preferred because these specifically infect antigen presenting cells (i.e. macrophages and dendritic cells). The viral vector may be attenuated or not attenuated. The nucleic acid sequence may be transformed into the viral or bacterial vector via a shuttle vector such as pKSV7 (1).

By "host cell" we mean a cell which is capable of expressing the target protein coded by the construct and in which cleavage of the target protein may occur intracellularly. Consequently, the host cells may be mammalian or insect cells in vitro, such as HEK293T cells, HELA cells, sf9 cells. Alternatively the host cells may be human or animal cells in vivo, which have been infected with a viral or bacterial vector containing a construct encoding the fusion protein, as a vaccine.

The expressed fusion protein is cleaved intracellularly by either a host protease or a protease encoded by the plasmid vector or a protease which is found in the viral or bacterial vector. The protease is selective for the cleavage sites. The vector may also encode an activator for the protease which is selective for the cleavage site. For example, the host protease may be non-active under normal conditions and become active only when the activator is expressed.

According to one embodiment the protease may be pathogen-specific. Accordingly, the nucleic acid may be designed such that protease cleavage sites may only be cleaved by a pathogen-specific protease. Then, the expressed fusion protein is only cleaved when the host cell is infected with a pathogen which produces a protease which is specific for the cleavage sites.

More specifically, the oligopeptides may be prepared in vivo as follows:

1. Design and Generation of the Synthetic Gene

A synthetic gene consisting of 20mer overlapping peptides from the original target gene can be designed with protease Factor Xa sites added in between the 20mer peptides. The resultant artificial gene can be optimised for bacterial expression and commercially synthesised before being cloned into prokaryotic expression vector, for example pET16, or a shuttle vector like pKSV7. A gene encoding the protease Factor Xa will also be cloned into the expression vector.

2. Production of Vectors which Encoding the Target Gene and/or the Genes Encoding Proteases which can Cut the Fusion Protein.

The construct with the artificial gene and the protease gene will be transformed into a attenuated or not attenuated *Listeria* vector. This may be administered as a vaccine. If the viral vector does not contain a protease gene, the vector may be administered in combination with a protease as a vaccine.

The invention also provides a fusion protein composed of overlapping peptides derived from a desired portion of a target protein interspersed with regions which code for protease cleavage sites and a nucleic acid sequence coding for the fusion protein.

The nucleic acid sequence encoding the fusion protein or the fusion protein itself may be used for the manufacture of a medicament for the prophylactic treatment of viral infections such as HIV, HCV, Herpes etc, or tumours such as melanoma, breast cancer, renal cancer, hepatic cancer, etc. Alternatively the medicament may be used for the treatment of a disease caused by a pathogen which produces a protease specific for the cleavage sites.

The invention also provides a method of treating a disease in a patient comprising:

treating the patient with a nucleic acid sequence encoding a fusion protein composed of overlapping peptides derived from a desired portion of a target protein interspersed with regions which code for protease cleavage sites, inducing expression of the fusion protein in the patient, whereby the expressed fusion protein is cleaved intracellularly by a protease which is specific for the cleavage sites; and a method of treating a disease in a patient comprising:

treating the patient with a fusion protein composed of overlapping peptides derived from a desired portion of a target protein interspersed with regions which code for protease cleavage sites, whereby the expressed fusion protein is cleaved intracellularly by a protease which is specific for the cleavage sites.

The disease to be treated may be a viral infection such as HIV, HCV, Herpes etc, or tumours such as melanoma, breast cancer, renal cancer, hepatic cancer, etc. Alternatively, the disease may be caused by a pathogen which produces a protease specific for the cleavage sites.

For example, an HIV fusion protein (e.g. Nef) with HIV protease substrate sites in between overlapping peptide sequences may be administered to a patient infected with HIV. The HIV protease present in the patient's body will cut the fusion protein into overlapping peptides which then will stimulate the immune system to kill the HIV infected cells.

The invention also provides a method of epitope mapping which comprises synthesising a family of oligopeptides of predetermined amino acid sequence, which together make up from 7 amino acids to the complete amino acid sequence of a target protein, which comprises:

synthesising a nucleic acid construct which codes for a fusion protein composed of overlapping peptides derived from the desired portion of the target protein, interspersed with regions which code for protease cleavage sites, expressing the nucleic acid construct in a suitable expression vector, harvesting the fusion protein corresponding to the nucleic acid sequence, and digesting the fusion protein with a protease selective for the cleavage sites to generate the oligopeptides and using these oligopeptides in an oligopeptide epitope mapping procedure.

EXAMPLE 1

The invention is now illustrated by reference to the following embodiment, carried out with HIV Nef protein
Methods:
1. DNA Design A synthetic gene was designed in such a way that it was composed of a series of 10-amino-acids overlapped 20mer peptides, interspersed with protease Factor Xa cleavage sites (Ile-Glu-Gly-Arg-; I-E-G-R-), covering the full length of the 206 amino acids Nef protein from Lai strain of Human Immunodeficiency Virus (HIV) (FIG. 1). The resulting artificial gene was optimised for *E. Coli*. Expression, and restrictive enzyme sites Nde I and Bam were added at the ends for subsequent subcloning and expression in pET16b vector.

2. Gene Synthesis

The gene was commercially synthesised by GeneArt, Regensburg, Germany.

3. Subcloning of the Target Gene into pET16b Expression Vector

The synthesised target gene, provided in a cloning vector pPCR-Script, was restrictively digested with Nde I and Bam HI. After agarose electrophoresis, the band corresponding to the target gene was sliced under ultraviolet light and the DNA was purified by QIAquick® Gel Extraction kit (Qiagen, Germany). Meanwhile, pET vector was digested with the same restrictive enzymes, ends de-phosphorylated with shrimp alkaline phosphatase (Roche, UK), and gel purified in the same way. The vector DNA and the target gene were ligated with T4 DNA ligase (New England Biolabs, UK) and the ligation product was transformed into DH5α bacteria. Colonies were inoculated from overnight LB agar plate culture and incubated in LB media with 100 mg/ml ampicillin. After overnight culture, plasmid DNA was extracted by QIAprep Spin Miniprep Kit (Qiagen, Germany), and sequenced to confirm correct insert.

4. Protein Expression

Miniprep DNA was transformed into BL21(DE3) bacteria, and colonies were inoculated and grown in low salt LB media overnight at 37° C. or 28° C. The culture were 1:100 diluted in low salt LB media and grown at 37° C. under shaking for several hours, until the bacteria reach exponential growth stage, as determined by OD600=0.3~0.5. One millimolar IPTG was be added to induce the protein expression. After 3~5 hours culturing with shaking at 37° C. or 28° C., bacteria were collected by spinning at 4000 rpm, then re-suspended in PBS, and lysed by sonication. The inclusion body, which contains the expressed protein, were collected by centrifugation.

5. Protein Purification

The expressed protein was purified by B-per (Pierce, UK) followed by Ni-NTA purification kit (Qiagen, Germany) according to the operation manual. Briefly, the inclusion bodies were re-suspended in denaturing buffer (8M Urea Tris buffer), and passed through the Ni-NTA column, to which the His-tagged protein binds. After extensive washing, protein was eluted by elution buffer, and buffer exchanged to Factor Xa digestion buffer (Tris buffer with 5 mM CaCl2) by passing through PD-10 column (Sephadex G-25).

6. Protease Digestion

Protein in digestion buffer was concentrated by Centriprep YM10 (Millipore, USA) and digested completely by incubating the protein with protease Factor Xa (New England Biolabs, UK) at room temperature for around 20 minutes. The protease was removed with benzamidine-agarose (Amersham Biosciences, USA) or simply through a YM10 filter tube, and the free His-tag will be removed with Ni-NTA agarose. The resulting mixture of oligopeptides will be concentrated and buffer-exchanged to PBS for further use.

7. Mass Spectrometer Analysis

The protease-digested product was analysed by mass spectrometry to confirm the digestion results in the desired overlapping peptides. Samples were carried out on an Applied Biosystems 4700 proteomics analyzer equipped with TOF/TOF ion optics and a diode pumped Nd:YAG laser with 200 Hz repetition rate. Generally, the width of mass window was set to 50 Da because the mass of precursor ion is less than 5000 Da, MS/MS data was acquired using the instrument default calibration, without applying internal or external calibration.

8. Mice and Immunization.

Inbred mice BALB/c ($H-2^d$) and C57BL/10 ($H-2^b$) were immunized with recombinant overlapping peptides at 5 µg of each individual peptide in 100 µl PBS per mouse together with MLP+TDM Adjuvant System. Control mice were given only adjuvant. Immunizations were given at weeks 0, 3, and 6. Three weeks after the last immunization, mice were sacrificed for CTL and T-helper cell proliferation assays.

Alternatively, randomly bred, outbred NMRI mice may be immunized subcutaneously (s.c.) with recombinant overlapping peptides at 5 µg of each individual peptide in 100 µl PBS per mouse together with or without MLP+TDM Adjuvant System 3 times at 3-week intervals. Control groups may be only given adjuvant or PBS. Another 3 weeks after the last boost, splenocytes may be collected and IFN-γ-specific ELISPOT assays and intracellular staining for IFN-γ may be performed.

9. Intracytoplasmic Cytokine Staining and Flow Cytometry Analysis.

Mouse splenocytes may be cultured at $5 \times 10^6$ cells/ml with IL-2 (20 U/ml) with or without 1 µM recombinant overlapping peptides in 24-well culture plates for 6 h. Four hours before harvesting, cells may be treated with Golgistop (BD PharMingen) according to the vendor's protocol. Splenocytes may be then stained with phycoerythrin-(PE)-conjugated monoclonal rat anti-mouse CD8 or CD4 antibody (BD PharMingen) or an immunoglobulin isotype control for 20 min. Splenocytes may be then subjected to intracellular cytokine staining using the Cytofix/Cytoperm kit (BD PharMingen) and FITC-conjugated anti-IFN-γ antibody (20 μg/ml) according to the manufacturer's instructions. Samples may be acquired on an Epics XL flow cytometer (Beckman Coulter, Fullerton, Calif.), and data may be analyzed using Expo 32 software (Beckman Coulter).

10. ELISPOT Assay.

ELISPOT assays were performed using ELISPOT kits from BD PharminGen. Briefly, splenocytes were restimulated overnight with 1 μM recombinant overlapping peptides in the IFN-γ-precoated plates. Cells were discarded and biotinylated anti-IFN-γ antibodies were added for 1 hour at 37° C. followed by another hour of incubation at 37° C. of anti-biotin antibody labelled with enzyme. After colour developed, spots were counted under a microscope. Results are expressed as SFU/10$^6$ cells.

11. Lymphocyte Proliferation Assay.

Splenocytes may be isolated and cultured at 2×10$^6$/ml in RPMI 1640 plus 15% FCS plus antibiotics in the presence of either HIV Nef protein (15 μg/ml), recombinant overlapping peptides (3 μg/ml) or OVA (15 μg/ml) for 5 days. Four hours before harvesting, cells may be pulsed with 1 μCi per well of $^3$H-thymidine. After cells are harvested, $^3$H-thymidine incorporation may be assessed using a β-counter (Beckman, Fullerton, Calif.). Results are expressed as stimulation index (SI), i.e., the ratio of cpm of stimulated cells to cpm of cells grown in medium only.

12. Rhesus Monkey Experiment

Four monkeys may be enrolled initially and different doses of recombinant overlapping peptides will be administered. IFN-γ-ELISPOT and proliferation assays may be performed to find an optimal dose to induce cellular immune responses.

Three groups of rhesus monkeys may be enrolled which will be given respectively; recombinant overlapping peptides (at the optimal dose), recombinant protein from which the overlapping peptides are generated at equivalent dose to the recombinant overlapping peptides, and PBS. IFN-γ-ELISPOT and proliferation assays will be performed to test if overlapping peptides can induce immune responses in the primate model.

Results of Example 1

Brief Description of Drawings

FIG. 1: A recombinant protein (SEQ ID NO:4) composed of 20 overlapping peptides covering Nef and a sort substrate sequence (in bold) of Factor Xa interspersed between each peptide, overlapping amino acid residues underlined;

FIG. 2: Purified (right) and unpurified (left) recombinant overlapping peptides (ROP) fusion protein (55 kd):

FIG. 4: ROP peptides and ROP protein taken up by DC2.4 cells, showing that oligopeptides were taken earlier than the protein.

FIG. 5: Uptaken ROP peptides (left) and ROP protein (right) by DC2.4 cells ROP peptides and ROP protein were labelled with green fluorescence while lysosomes were stained with LysoTracker-red. Note; in the right picture, the green labelled protein are co-localized with the red stained lysosomes.

Results

A recombinant protein composed of 20 overlapping peptides covering Nef protein was made (ROP protein) and a short substrate sequence of the protease factor Xa was interspersed between each peptide (FIG. 1).

Figure 3A:
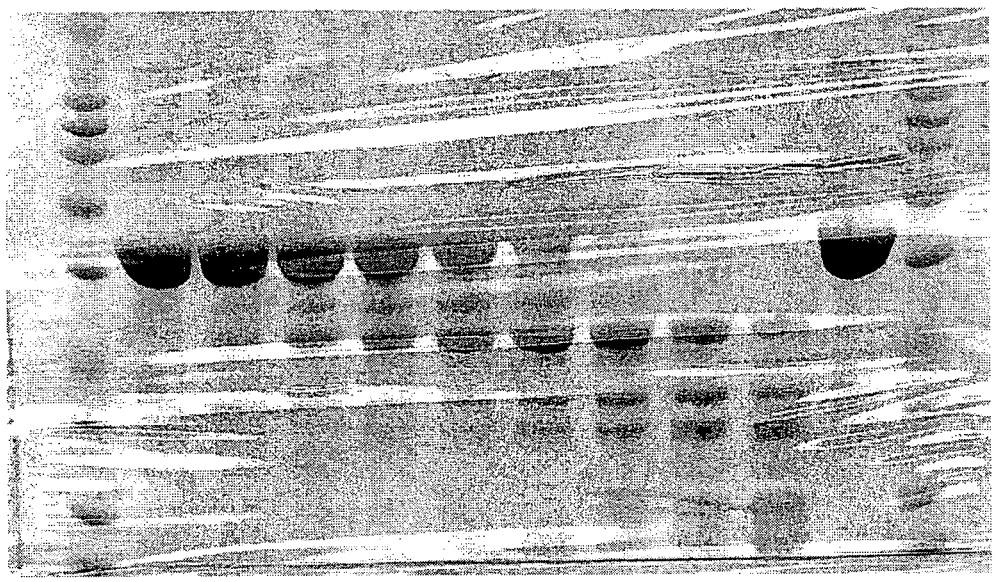
FIG. 3: SDS page and Mass spectrometry profile of ROP peptides after digesting ROP protein by Factor Xa.
  (a): titration of Factor Xa. 100 μl ROP protein (2.2 mg/ml) incubated with series of two fold diluted Factor Xa. Ln 0: no Factor Xa; Ln 1: 1 μl (2 unit/μl); Ln 2: ½ μl; Ln 3: ¼ μl; ... Ln 9: 1/256 μl;
  (b): Mass Spectrometry of digested ROP. The responses were at 4° C. 1 hour.
Figure 3B:
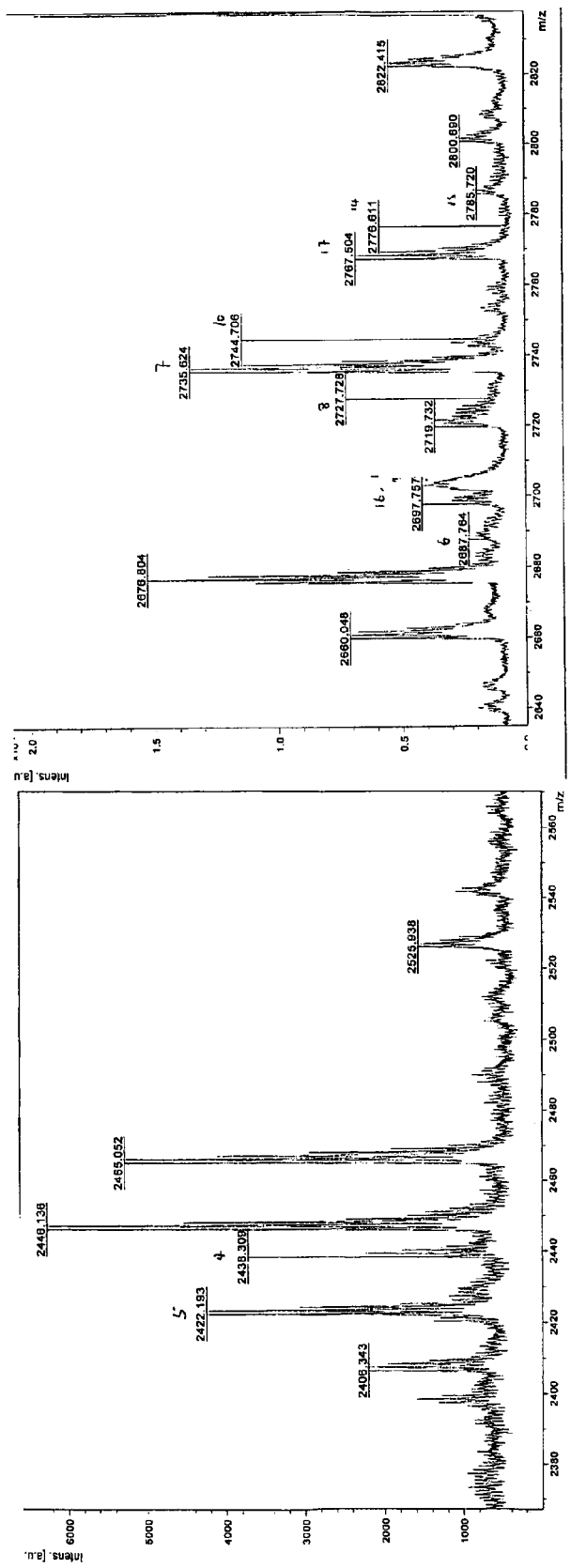

After the purification (FIG. 2), the ROP protein was cut by Factor Xa into overlapping peptides (ROP peptides) as shown in the mass spectrometry (FIG. 3).

The way that mouse dendritic cells (DC) taking ROP protein and ROP peptides (both labelled with green fluorescence) was compared. It appeared that ROP peptides were taken up by the DC quicker (started from 5 minutes) than ROP protein (FIG. 4) and most of the peptides (labelled with green fluorescence) went directly into the cytoplasma; while the ROP protein (labelled with green fluorescence) went to lysosomes (stained with red colour) (FIG. 5).

Figure 6:
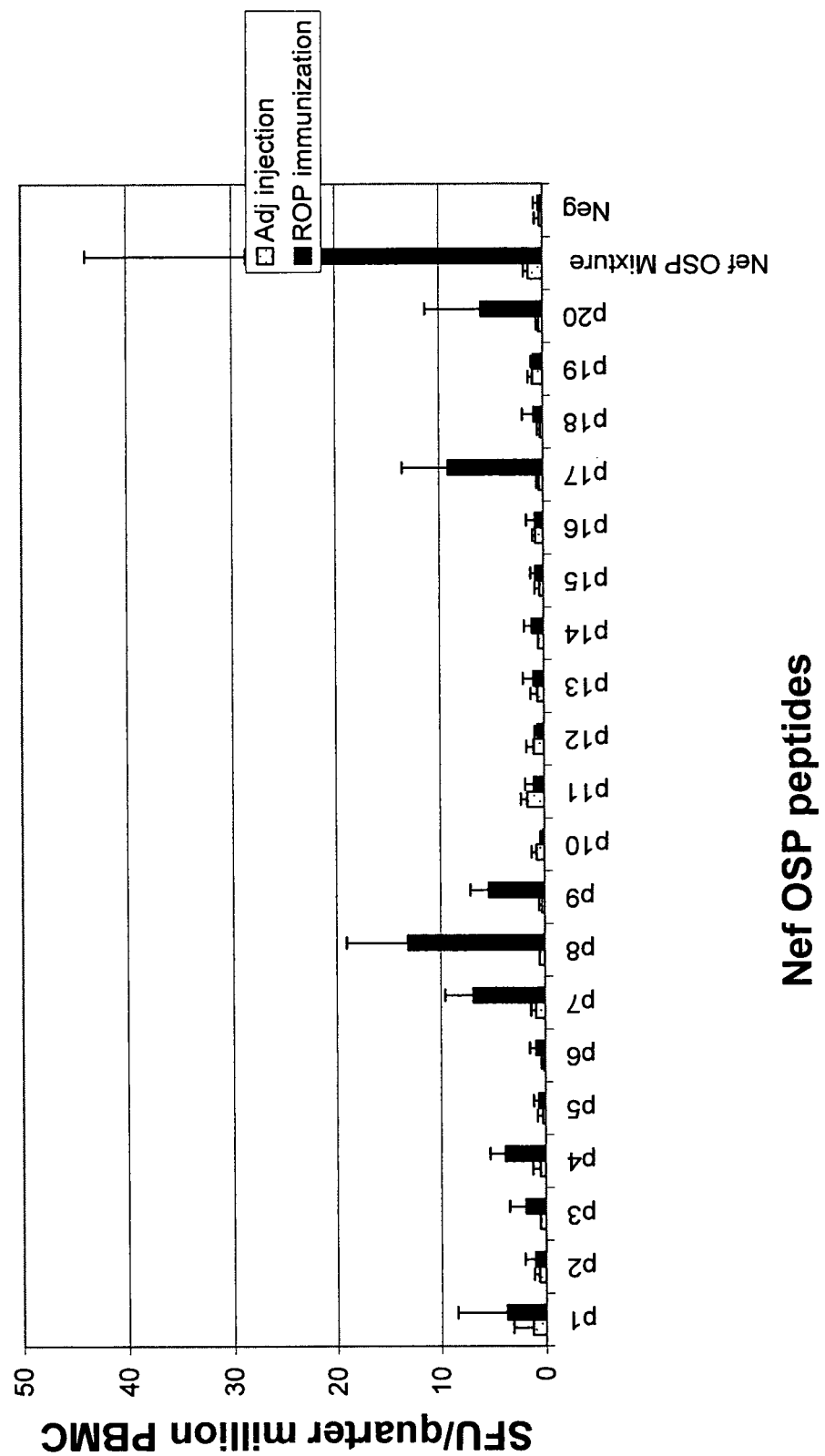
FIG. 6: Immunization of two different strains of mice with ROP peptides generated immune responses to the peptides, in different strains of mice the immune response target different individual peptides within the pool of overlapping peptides.
Figure 6:
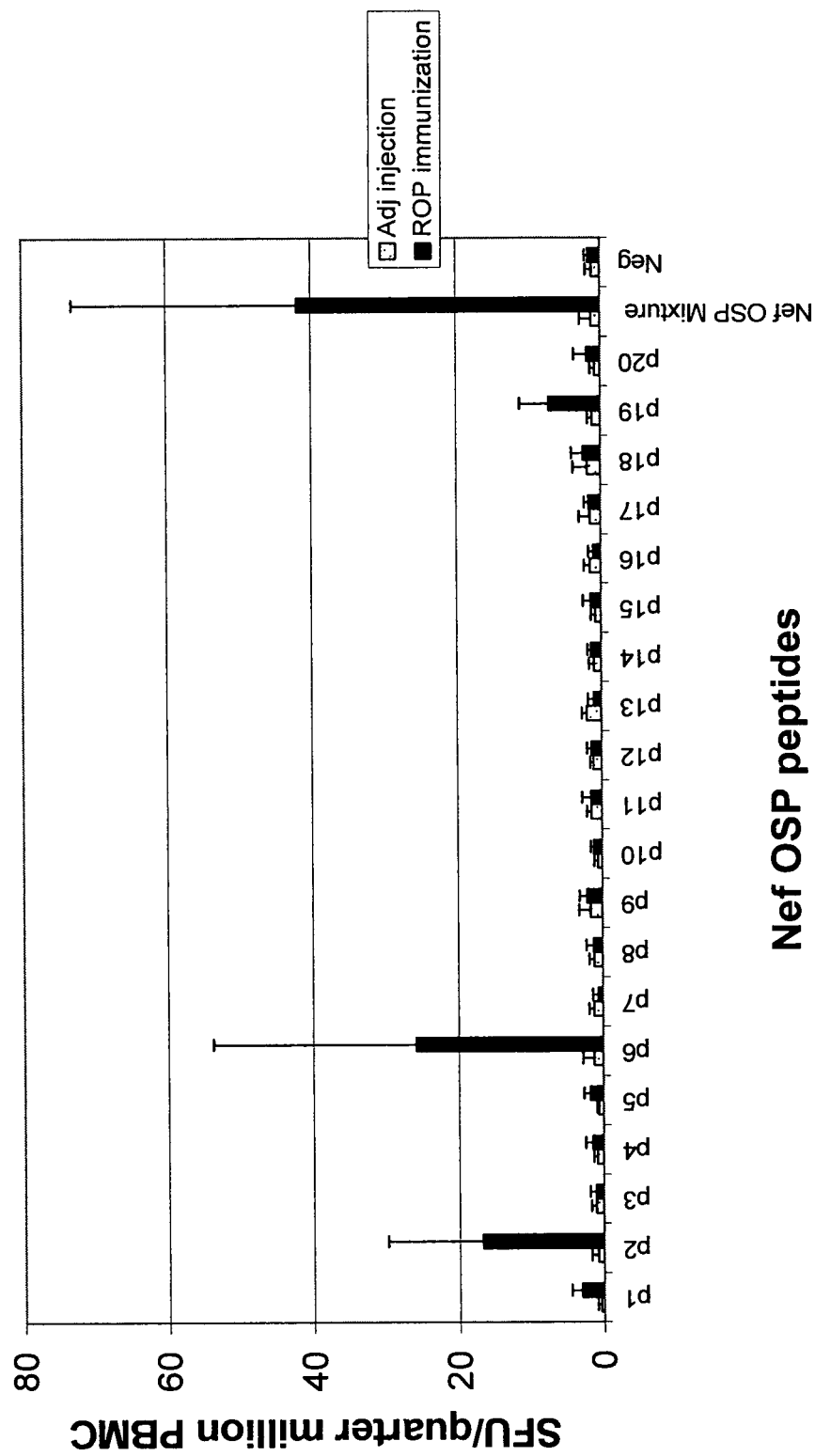

Immunization of two different strains of mice with ROP peptides generated immune responses to the peptides as well as to the ROP protein in both strains of mice. Nevertheless, in different strains of mice the immune response target different individual peptides within the pool of overlapping peptides (FIG. 6).

| Sequences (SEQ ID NO:) | HIV Nef (strains) | Mouse Position | strains |
|---|---|---|---|
| CD4 Epitopes from database | | | |
| MGGKWSKSSVVGWPTVRERM (8) | Nef(Lai) | 1-20 | H-2$^d$ |
| MGGKWSKSSVIGWPTVRERM (9) | Nef(HXB2) | 1-20 | H-2$^d$ |
| VRERMRRAEPAADGVGAASR (10) | Nef(Lai) | 16-35 | H-2$^d$ |
| GAASRDLEKHGAITSSNTAA (11) | Nef(Lai) | 31-50 | H-2$^d$ |
| SNTAATNAACAWLEAQEEEE (12) | Nef(BRU) | 46-65 | H-2$^d$ |
| SSNTAATNAACAWLEAQEEEEVG FP (13) | | 46-69 | |
| QEEEEVGFPVTPQVPLRPMT (14) | Nef(Lai) | 61-80 | H-2$^b$ |
| *LRPMTYKAAVDLSHFLKEKG* (15) | | | |
| VGFPV*TPQVPLRPMTYKAAVDLS HFLKEKGGL* (16) | Nef(Lai) | 76-95 | H-2$^b$ |

-continued

| Sequences (SEQ ID NO:) | HIV Nef (strains) | Mouse Position strains |
|---|---|---|
| LKEKGGLEGLIHSQRRQDIL (17) | Nef(Lai) | 91-110 H-2$^b$ |
| RQDILDLWIYHTQGYFPDWQ (18) | Nef(Lai) | 106-125 H-2$^b$ |
| FPDWQNYTPGPGVRYPLTFG (19) | Nef(Lai) | 121-140 H-2$^b$ |
| PLTFGWCYKLVPVEPDKVEE (20) | Nef(Lai) | 136-155 H-2$^d$ |
| DKVEEANKGENTSLLHPVSL (21) | Nef(Lai) | 151-170 H-2$^d$ |
| HPVSLHGMDDPEREVLEWRF (22) | Nef(Lai) | 166-185 H-2$^{b,d}$ |
| CD8 ROP epitopes | | |
| TAATNADCA (23) | Nef(HXB2) | 48-56 H-2$^b$ |
| GVRYPLTFGWCYKLVP (24) | Nef(Lai) | 132-147 H-2$^d$ |
| EWRFDSRLAFHHVAREL (25) | Nef(HXB2) | 182-198 H-2$^d$ |
| QEEEEVGFPVTPQVPLRPMT (14) | Nef Lai | 61-80 H-2$^b$ |
| TPQVP*LRPM*TYKA*SVDLSHF* (26) | Nef Lai | 71-90 H-2$^b$ |
| YKAAVDLSHF<u>LKEKGGLEGL</u> (27) | Nef Lai | 81-100 H-2$^b$ |
| NTRLLHPVSLHGMDDPEREV (28) | Nef Lai | 161-180 H-2$^b$ |
| FHHVARELHPEY (29) | Nef Lai | 191-202 H-2$^b$ |
| VGWPAVRERMRRAEPAADGV (30) | Nef Lai | 20-40 H-2$^d$ |
| TNADCAWLEAQEEEEVGFPV (31) | Nef Lai | 51-70 H-2$^d$ |

ROP epitopes were compared with epitopes from HIV Molecular Immunology Database (http://hiv-vacdb.lanl.gov/content/immonology/tables/ctl_summary.html). Three of the epitopes from H-2$^b$ mice were either exactly the same or overlap with the known epitopes (showed in bold, italic or underlined).

These results show that immunization with recombinant overlapping peptides (ROP) (containing IEGR), generated immune responses to HIV Nef. In another words, the recombinant overlapping peptides (containing IEGR) immunized cells in the mouse body responded to viral elements containing Nef which has been tested by overlapping synthetic peptides.

Epitopes identified in this way can be the same as the epitope in the HIV Molecular Immunology Database (http://hiv-vacdb.lanl.gov/contentimmunology/tables/ctl_summary.html); partially the same as that in the database; or totally different. Activity was compared with synthetic peptides (overlapping synthetic peptides covering Nef Lai sequence) supplied by Sigma-Genosys, which did not contain the did not contain IEGR sequence.

It can be concluded that IEGR does not affect the ability of recombinant overlapping peptides (ROP) to stimulate Nef specific immune response.

Figure 7:
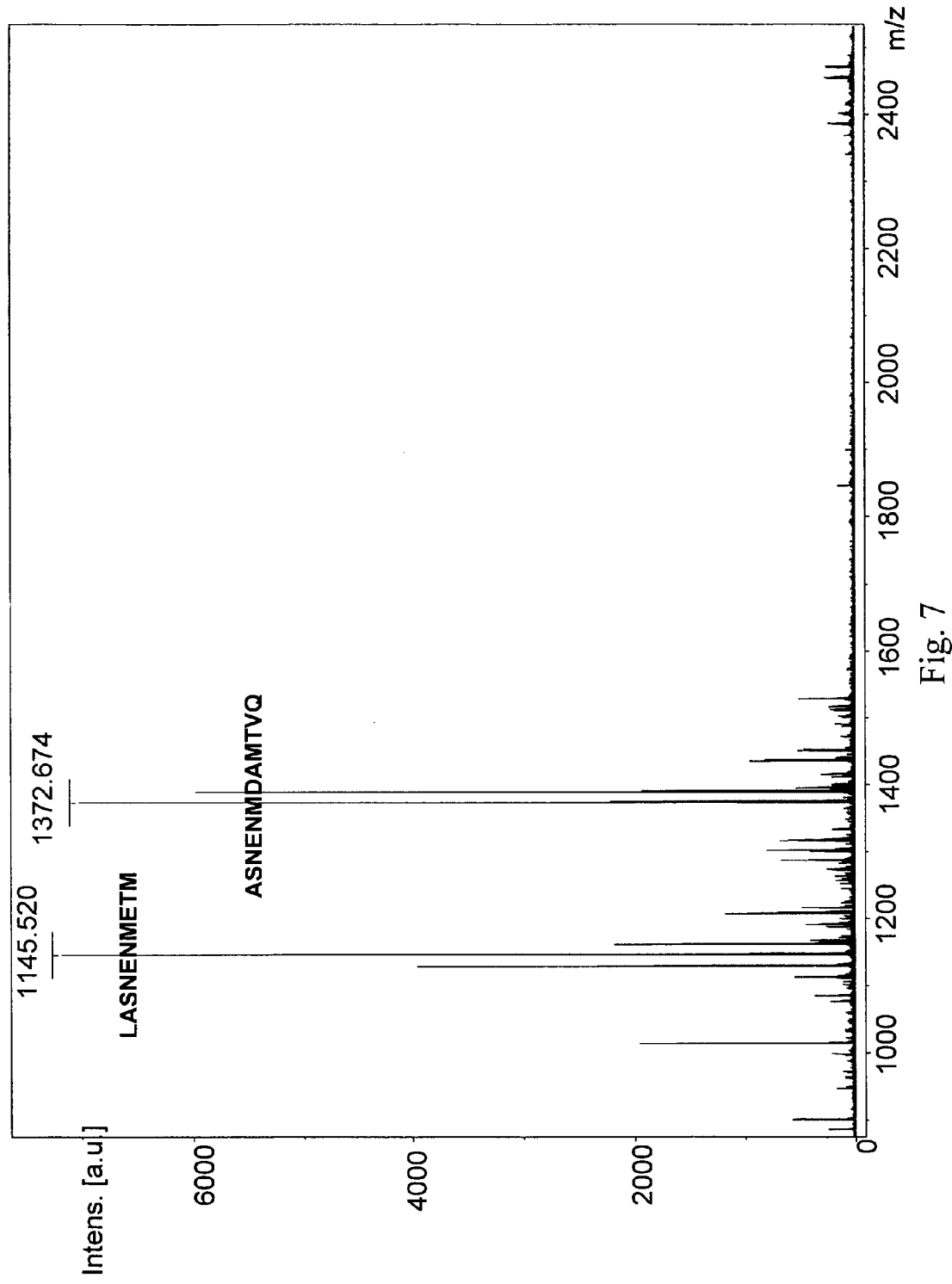
FIG. 7: Peptide ASNENMDAM TQV/L ASNENMETH (SEQ ID NO:5) was incubated at 37° C. for 30 minutes with 5 mU Cathepsin S (Calbiochem). The enzyme reaction was terminated by heating up at 100° C. for 5 minutes. The products were filtered through Millipore Microcon centrifugal filter (YM-10) to separate peptides from the enzyme, which were analysed by mass spectrometry. The peptide was cleaved into two peptides: ASNENMDAM TVQ (SEQ ID NO:6) and LASNENMETH (SEQ ID NO:7).

In further experiments, a cathepsin S cleavage site (TQV/L (SEQ ID NO:3)) was introduced into a peptide sequence. This was successfully cleaved in vitro using cathepsin S under conventional conditions and the two fragments characterised by MS (FIG. 7).

EXAMPLE 2

The invention is now illustrated by reference to the following embodiment, carried out with HIV Nef protein
Methods:
1. DNA Design
A synthetic gene will be designed in such a way that it is composed of a series of 10-amino-acids overlapped 20mer peptides, interspersed with protease tryptase or cathepsin S cleavage sites, covering the full length of the 202 amino acids Nef protein from Lai strain of Human Immunodeficiency Virus (HIV).
2. Gene Synthesis
The gene will be commercially synthesised by GeneArt, Regensburg, Germany.
3. Making Live Attenuated Vector Vaccines
A recombinant live attenuated vector vaccine will be constructed, *Listeria*-overlapping Nef, by a stable modification of its chromosomes using the shuttle vector pKSV7 (1) and a protocol modified from Camilli et al. (2), as described previously (3), to insert HIV-gag into the sepA gene of *L. monocytogenes*.
4. Mice and Immunization.
Different strains of inbred and/or outbred mice will be immunized subcutaneously (s.c.) with attenuated *Listeria*-overlapping Nef 10$^6$-10$^7$ pfu per mouse once or twice with 2-4 week's interval. Control groups will be only given *Listeria* only or PBS. One-two weeks after the last boost, splenocytes will be collected and IFN-γ-specific ELISPOT assays and intracellular staining for IFN-γ will be performed.
5. Intracytoplasmic Cytokine Staining and Flow Cytometry Analysis.
Mouse splenocytes will be cultured at 5×10$^6$ cells/ml with IL-2 (20 U/ml) with or without 1 μM recombinant overlapping peptides in 24-well culture plates for 6 h. Four hours before harvesting, cells will be treated with Golgistop (BD PharMingen) according to the vendor's protocol. Splenocytes will be then stained with phycoerythrin-(PE)-conjugated monoclonal rat anti-mouse CD8 or CD4 antibody (BD PharMingen) or an immunoglobulin isotype control for 20 min. Splenocytes will be then subjected to intracellular cytokine staining using the Cytofix/Cytoperm kit (BD PharMingen) and FITC-conjugated anti-IFN-γ antibody (20 μg/ml) according to the manufacturer's instructions. Samples will be acquired on an Epics XL flow cytometer (Beckman Coulter, Fullerton, Calif.), and data will be analyzed using Expo 32 software (Beckman Coulter).
6. ELISPOT Assay.
ELISPOT assays will be performed using ELISPOT kits from BD PharminGen. Briefly, splenocytes will be restimulated overnight with 1 μM recombinant overlapping peptides in the IFN-γ-precoated plates. Cells will be discarded and biotinylated anti-IFN-γ. antibodies will be added for 1 hour at 37° C. followed by another hour of incubation at 37° C. of anti-biotin antibody labelled with enzyme. After colour developed, spots will be counted under a microscope. Results are expressed as SFU/10$^6$ cells.
7. Lymphocyte Proliferation Assay.
Splenocytes will be isolated and cultured at 2×10$^6$/ml in RPMI 1640 plus 15% FCS plus antibiotics in the presence of either HIV Nef protein (15 μg/ml), recombinant overlapping peptides (3 μg/ml) or OVA (15 μg/ml) for 5 days. Four hours before harvesting, cells were pulsed with 1 μCi per well of $^3$H-thymidine. After cells were harvested, $^3$H-thymidine incorporation was assessed using a β-counter (Beckman, Fullerton, Calif.). Results are expressed as stimulation index (SI), i.e., the ratio of cpm of stimulated cells to cpm of cells grown in medium only.

8. Rhesus Monkey Experiment

Four monkeys will be enrolled initially and different doses of recombinant *Listeria*-overlapping Nef (*Listeria* expressing Nef and *Listeria* only as control) will be administered. IFN-γ-ELISPOT and proliferation assays will be performed to find an optimal dose to induce cellular immune responses.

Three groups of rhesus monkeys will be enrolled which will be given respectively; *Listeria*-overlapping Nef (at the optimal dose), *Listeria*-Nef and *Listeria* only. IFN-γ-ELISPOT and proliferation assays will be performed to test if overlapping peptides can induce immune responses in the primate model.

9. Experiments of Dendritic Cells (DC) Taking Up Peptides and Protein.

Mouse DC cell lines DC2.4 will be used to observe how DC cells taking up the recombinant overlapping peptides (ROP peptides) and its corresponding recombinant protein (ROP protein). Both ROP peptides and protein will be labelled using Invitrogen LIVE/DEAD® Fixable Dead Cell Stain Kits (green-fluorescent reactive dye—cat no L23101). The green fluorescent dye can be bound to amines of peptides or proteins. Free fluorescence does not permeate into live cells. However the peptides or proteins bound with fluorescence can be taken up by live dendritic cells which will become green. This can be measured by flowcytometry or observed under confocal microscopy.

REFERENCES

1. Smith, K., and P. Youngman. 1992. Use of a new integrational vector to investigate compartment-specific expression of the *Bacillus subtilis* spoIIM gene. *Biochimie* 74:705.
2. Camilli, A., L. G. Tilney, and D. A. Portnoy. 1993. Dual roles of plcA in *Listeria monocytogenes* pathogenesis. *Mol Microbiol* 8:143.
3. Thompson, R. J., H. G. Bouwer, D. A. Portnoy, and F. R. Frankel. 1998. Pathogenicity and immunogenicity of a *Listeria monocytogenes* strain that requires D-alanine for growth. *Infect Immun* 66:3552.

The invention claimed is:

1. A fusion protein composed of overlapping oligopeptides derived from a desired portion of a target protein which fusion protein is at least 100 amino acids long interspersed with regions which code for protease cleavage sites, wherein each of the interspersed regions codes for the same protease cleavage site, wherein the overlapping oligopeptides are 10 to 30 amino acids long each with a 5 to 25 amino acid overlap with the adjacent overlapping peptide, and wherein the overlapping peptides together span the amino acid sequence of the desired portion of the target protein and the fusion protein is composed of 5 or more overlapping oligopeptides, and wherein (a) each overlapping oligopeptide maintains an amino acid sequence derived from the protease cleavage site or (b) if the protease cleavage site is cut by a protease after said site, each overlapping oligopeptide except the most C-terminal overlapping oligopeptide maintains an amino acid sequence derived from the protease cleavage site, wherein the protease cleavage site is a cathepsin S cleavage site or a factor Xa digestion site.

2. The fusion protein of claim 1, wherein the fusion protein is composed of 10 or more overlapping oligopeptides.

3. The fusion protein of claim 1, wherein the protease cleavage site is a Factor Xa digestion site Ile-Glu-Gly-Arg or cathepsin sequence TVQ/L, wherein "/L" represents the cutting site.

4. The fusion protein of claim 1, wherein the desired portion is a coat protein of a virus or an enzyme characteristic of the virus, a carcinoembryonic antigen, or a Her2/neu antigen.

5. The fusion protein of claim 1, wherein the desired portion is at least 200 amino acids long.

6. The fusion protein of claim 1, wherein the overlapping peptides together make up from 75% to 100% of the complete amino acid sequence of the target protein.

7. The fusion protein of claim 1, wherein the oligopeptides are of equal length.

8. A mixture comprising overlapping oligopeptides made from the fusion protein of claim 1, wherein the mixture is made by a process comprising the following steps:

providing the fusion protein according to claim 6; and cutting the fusion protein in vitro with a protease being selective for the cleavage sites, thereby forming a cleavaged mixture containing the overlapping oligopeptides.

9. The mixture of claim 8, wherein the cutting is incubating the fusion protein with protease Factor Xa at room temperature for about 20 minutes.

10. A family of overlapping oligopeptides which is made from the fusion protein of claim 1 by cutting the fusion protein in vitro with a protease being selective for the cleavage site.

11. A pharmaceutical composition which comprises the family of overlapping oligopeptides of claim 10 and pharmaceutically acceptable carrier.

* * * * *

SEQUENCE LISTING

```
<160> NUMBER OF SEQ ID NOS: 31

<210> SEQ ID NO 1
<211> LENGTH: 4
<212> TYPE: PRT
<213> ORGANISM: Artificial
<220> FEATURE:
<223> OTHER INFORMATION: Factor Xa digestion site

<400> SEQUENCE: 1

Ile Glu Gly Arg
1

<210> SEQ ID NO 2
<211> LENGTH: 8
<212> TYPE: PRT
<213> ORGANISM: Artificial
<220> FEATURE:
<223> OTHER INFORMATION: HRV 3 C protease cleavage site

<400> SEQUENCE: 2

Leu Glu Val Leu Phe Gln Gly Pro
1               5

<210> SEQ ID NO 3
<211> LENGTH: 4
<212> TYPE: PRT
<213> ORGANISM: Artificial
<220> FEATURE:
<223> OTHER INFORMATION: Cathespin S sequence

<400> SEQUENCE: 3

Thr Val Gln Leu
1

<210> SEQ ID NO 4
<211> LENGTH: 325
<212> TYPE: PRT
<213> ORGANISM: Artificial
<220> FEATURE:
<223> OTHER INFORMATION: Recombinant protein comprising overlapping
``` peptides of HIV nef with Factor Xa cleavage sites inserted therein

<400> SEQUENCE: 4

Met Gly Gly Lys Trp Ser Lys Ser Ser Val Val Gly Trp Pro Ala Val
1               5                   10                  15

Arg Glu Arg Met Ile Glu Gly Arg Val Gly Trp Pro Ala Val Arg Glu
            20                  25                  30

Arg Met Arg Arg Ala Glu Pro Ala Ala Asp Gly Val Ile Glu Gly Arg
        35                  40                  45

Arg Arg Ala Glu Pro Ala Ala Asp Gly Val Gly Ala Val Ser Arg Asp
50                  55                  60

Leu Glu Lys His Ile Glu Gly Arg Gly Ala Val Ser Arg Asp Leu Glu
65                  70                  75                  80

Lys His Gly Ala Ile Thr Ser Ser Asn Thr Ala Ala Ile Glu Gly Arg
                85                  90                  95

Gly Ala Ile Thr Ser Ser Asn Thr Ala Ala Thr Asn Ala Asp Cys Ala
            100                 105                 110

Trp Leu Glu Ala Ile Glu Gly Arg Thr Asn Ala Asp Cys Ala Trp Leu
            115                 120                 125

Glu Ala Gln Glu Glu Glu Val Gly Phe Pro Val Ile Glu Gly Arg
            130                 135                 140

Gln Glu Glu Glu Val Gly Phe Pro Val Thr Pro Gln Val Pro Leu
145                 150                 155                 160

Arg Pro Met Thr Ile Glu Gly Arg Thr Pro Gln Val Pro Leu Arg Pro
            165                 170                 175

Met Thr Tyr Lys Ala Ala Val Asp Leu Ser His Phe Ile Glu Gly Arg
            180                 185                 190

Tyr Lys Ala Ala Val Asp Leu Ser His Phe Leu Lys Glu Lys Gly Gly
            195                 200                 205

Leu Glu Gly Leu Ile Glu Gly Arg Leu Lys Glu Lys Gly Gly Leu Glu
            210                 215                 220

Gly Leu Ile His Ser Gln Arg Arg Gln Asp Ile Leu Ile Glu Gly Arg
225                 230                 235                 240

Ile His Ser Gln Arg Arg Gln Asp Ile Leu Asp Leu Trp Ile Tyr His
                245                 250                 255

Thr Gln Gly Tyr Ile Glu Gly Arg Asp Leu Trp Ile Tyr His Thr Gln
            260                 265                 270

Gly Tyr Phe Pro Asp Trp Gln Asn Tyr Thr Pro Glu Ile Glu Gly Arg
            275                 280                 285

Phe Pro Asp Trp Gln Asn Tyr Thr Pro Glu Pro Gly Val Arg Tyr Pro
            290                 295                 300

Leu Thr Phe Gly Ile Glu Gly Arg Pro Gly Val Arg Tyr Pro Leu Thr
305                 310                 315                 320

Phe Gly Trp Cys Tyr
                325

<210> SEQ ID NO 5
<211> LENGTH: 22
<212> TYPE: PRT
<213> ORGANISM: Artificial
<220> FEATURE:
<223> OTHER INFORMATION: Recombinant peptide comprising overlapping
      sequences derived from influenza A virus nucleocapsid protein with
      Factor Xa cleavage site inserted therein

<400> SEQUENCE: 5

Ala Ser Asn Glu Asn Met Asp Ala Met Thr Gln Val Leu Ala Ser Asn
1               5                   10                  15

Glu Asn Met Glu Thr His
            20

<210> SEQ ID NO 6
<211> LENGTH: 12
<212> TYPE: PRT
<213> ORGANISM: Artificial
<220> FEATURE:
<223> OTHER INFORMATION: Recombinant peptide comprising sequence derived
      from influenza A virus nucleocapsid protein with cleaved Factor Xa
      cleavage site at C terminus

<400> SEQUENCE: 6

Ala Ser Asn Glu Asn Met Asp Ala Met Thr Val Gln
1               5                   10

<210> SEQ ID NO 7
<211> LENGTH: 10
<212> TYPE: PRT
<213> ORGANISM: Artificial
<220> FEATURE:
<223> OTHER INFORMATION: Recombinant peptide comprising overlapping
      sequences derived from influenza A virus nucleocapsid protein with
      cleaved Factor Xa cleavage site at N terminus

<400> SEQUENCE: 7

Leu Ala Ser Asn Glu Asn Met Glu Thr His
1               5                   10

<210> SEQ ID NO 8
<211> LENGTH: 20
<212> TYPE: PRT
<213> ORGANISM: Human immunodeficiency virus

<400> SEQUENCE: 8

Met Gly Gly Lys Trp Ser Lys Ser Ser Val Val Gly Trp Pro Thr Val
1               5                   10                  15

Arg Glu Arg Met
            20

<210> SEQ ID NO 9
<211> LENGTH: 20
<212> TYPE: PRT
<213> ORGANISM: Human immunodeficiency virus

<400> SEQUENCE: 9

Met Gly Gly Lys Trp Ser Lys Ser Ser Val Ile Gly Trp Pro Thr Val
1               5                   10                  15

Arg Glu Arg Met
            20

<210> SEQ ID NO 10
<211> LENGTH: 20
<212> TYPE: PRT
<213> ORGANISM: Human immunodeficiency virus

<400> SEQUENCE: 10

Val Arg Glu Arg Met Arg Arg Ala Glu Pro Ala Ala Asp Gly Val Gly
1               5                   10                  15

Ala Ala Ser Arg
            20

```
<210> SEQ ID NO 11
<211> LENGTH: 20
<212> TYPE: PRT
<213> ORGANISM: Human immunodeficiency virus

<400> SEQUENCE: 11

Gly Ala Ala Ser Arg Asp Leu Glu Lys His Gly Ala Ile Thr Ser Ser
1               5                   10                  15

Asn Thr Ala Ala
            20

<210> SEQ ID NO 12
<211> LENGTH: 20
<212> TYPE: PRT
<213> ORGANISM: Human immunodeficiency virus

<400> SEQUENCE: 12

Ser Asn Thr Ala Ala Thr Asn Ala Ala Cys Ala Trp Leu Glu Ala Gln
1               5                   10                  15

Glu Glu Glu Glu
            20

<210> SEQ ID NO 13
<211> LENGTH: 25
<212> TYPE: PRT
<213> ORGANISM: Human immunodeficiency virus

<400> SEQUENCE: 13

Ser Ser Asn Thr Ala Ala Thr Asn Ala Ala Cys Ala Trp Leu Glu Ala
1               5                   10                  15

Gln Glu Glu Glu Glu Val Gly Phe Pro
            20                  25

<210> SEQ ID NO 14
<211> LENGTH: 20
<212> TYPE: PRT
<213> ORGANISM: Human immunodeficiency virus

<400> SEQUENCE: 14

Gln Glu Glu Glu Glu Val Gly Phe Pro Val Thr Pro Gln Val Pro Leu
1               5                   10                  15

Arg Pro Met Thr
            20

<210> SEQ ID NO 15
<211> LENGTH: 20
<212> TYPE: PRT
<213> ORGANISM: Human immunodeficiency virus

<400> SEQUENCE: 15

Leu Arg Pro Met Thr Tyr Lys Ala Ala Val Asp Leu Ser His Phe Leu
1               5                   10                  15

Lys Glu Lys Gly
            20

<210> SEQ ID NO 16
<211> LENGTH: 32
<212> TYPE: PRT
<213> ORGANISM: Human immunodeficiency virus

<400> SEQUENCE: 16

Val Gly Phe Pro Val Thr Pro Gln Val Pro Leu Arg Pro Met Thr Tyr
1               5                   10                  15
```

Lys Ala Ala Val Asp Leu Ser His Phe Leu Lys Glu Lys Gly Gly Leu
            20                  25                  30

<210> SEQ ID NO 17
<211> LENGTH: 20
<212> TYPE: PRT
<213> ORGANISM: Human immunodeficiency virus

<400> SEQUENCE: 17

Leu Lys Glu Lys Gly Gly Leu Glu Gly Leu Ile His Ser Gln Arg Arg
1               5                   10                  15

Gln Asp Ile Leu
            20

<210> SEQ ID NO 18
<211> LENGTH: 20
<212> TYPE: PRT
<213> ORGANISM: Human immunodeficiency virus

<400> SEQUENCE: 18

Arg Gln Asp Ile Leu Asp Leu Trp Ile Tyr His Thr Gln Gly Tyr Phe
1               5                   10                  15

Pro Asp Trp Gln
            20

<210> SEQ ID NO 19
<211> LENGTH: 20
<212> TYPE: PRT
<213> ORGANISM: Human immunodeficiency virus

<400> SEQUENCE: 19

Phe Pro Asp Trp Gln Asn Tyr Thr Pro Gly Pro Gly Val Arg Tyr Pro
1               5                   10                  15

Leu Thr Phe Gly
            20

<210> SEQ ID NO 20
<211> LENGTH: 20
<212> TYPE: PRT
<213> ORGANISM: Human immunodeficiency virus

<400> SEQUENCE: 20

Pro Leu Thr Phe Gly Trp Cys Tyr Lys Leu Val Pro Val Glu Pro Asp
1               5                   10                  15

Lys Val Glu Glu
            20

<210> SEQ ID NO 21
<211> LENGTH: 20
<212> TYPE: PRT
<213> ORGANISM: Human immunodeficiency virus

<400> SEQUENCE: 21

Asp Lys Val Glu Glu Ala Asn Lys Gly Glu Asn Thr Ser Leu Leu His
1               5                   10                  15

Pro Val Ser Leu
            20

<210> SEQ ID NO 22
<211> LENGTH: 20
<212> TYPE: PRT
<213> ORGANISM: Human immunodeficiency virus

<400> SEQUENCE: 22

His Pro Val Ser Leu His Gly Met Asp Asp Pro Glu Arg Glu Val Leu
1               5                   10                  15

Glu Trp Arg Phe
            20

<210> SEQ ID NO 23
<211> LENGTH: 9
<212> TYPE: PRT
<213> ORGANISM: Human immunodeficiency virus

<400> SEQUENCE: 23

Thr Ala Ala Thr Asn Ala Asp Cys Ala
1               5

<210> SEQ ID NO 24
<211> LENGTH: 16
<212> TYPE: PRT
<213> ORGANISM: Human immunodeficiency virus

<400> SEQUENCE: 24

Gly Val Arg Tyr Pro Leu Thr Phe Gly Trp Cys Tyr Lys Leu Val Pro
1               5                   10                  15

<210> SEQ ID NO 25
<211> LENGTH: 17
<212> TYPE: PRT
<213> ORGANISM: Human immunodeficiency virus

<400> SEQUENCE: 25

Glu Trp Arg Phe Asp Ser Arg Leu Ala Phe His His Val Ala Arg Glu
1               5                   10                  15

Leu

<210> SEQ ID NO 26
<211> LENGTH: 20
<212> TYPE: PRT
<213> ORGANISM: Human immunodeficiency virus

<400> SEQUENCE: 26

Thr Pro Gln Val Pro Leu Arg Pro Met Thr Tyr Lys Ala Ser Val Asp
1               5                   10                  15

Leu Ser His Phe
            20

<210> SEQ ID NO 27
<211> LENGTH: 20
<212> TYPE: PRT
<213> ORGANISM: Human immunodeficiency virus

<400> SEQUENCE: 27

Tyr Lys Ala Ala Val Asp Leu Ser His Phe Leu Lys Glu Lys Gly Gly
1               5                   10                  15

Leu Glu Gly Leu
            20

<210> SEQ ID NO 28
<211> LENGTH: 20
<212> TYPE: PRT
<213> ORGANISM: Human immunodeficiency virus

<400> SEQUENCE: 28

```
Asn Thr Arg Leu Leu His Pro Val Ser Leu His Gly Met Asp Asp Pro
1               5                   10                  15

Glu Arg Glu Val
            20

<210> SEQ ID NO 29
<211> LENGTH: 12
<212> TYPE: PRT
<213> ORGANISM: Human immunodeficiency virus

<400> SEQUENCE: 29

Phe His His Val Ala Arg Glu Leu His Pro Glu Tyr
1               5                   10

<210> SEQ ID NO 30
<211> LENGTH: 20
<212> TYPE: PRT
<213> ORGANISM: Human immunodeficiency virus

<400> SEQUENCE: 30

Val Gly Trp Pro Ala Val Arg Glu Arg Met Arg Arg Ala Glu Pro Ala
1               5                   10                  15

Ala Asp Gly Val
            20

<210> SEQ ID NO 31
<211> LENGTH: 20
<212> TYPE: PRT
<213> ORGANISM: Human immunodeficiency virus

<400> SEQUENCE: 31

Thr Asn Ala Asp Cys Ala Trp Leu Glu Ala Gln Glu Glu Glu Glu Val
1               5                   10                  15

Gly Phe Pro Val
            20
```